United States Patent [19]

Blohm et al.

[11] 4,187,319
[45] * Feb. 5, 1980

[54] SUBSTITUTED BENZALDEHYDE HYPOLIPIDEMIC AGENTS

[75] Inventors: Thomas R. Blohm, Maderia; J. Martin Grisar; Roger A. Parker, both of Cincinnati, all of Ohio

[73] Assignee: Richardson-Merrell Inc., Wilton, Conn.

[*] Notice: The portion of the term of this patent subsequent to Jan. 3, 1995, has been disclaimed.

[21] Appl. No.: 802,853

[22] Filed: Jun. 2, 1977

Related U.S. Application Data

[63] Continuation of Ser. No. 619,304, Oct. 3, 1975, Pat. No. 4,066,788.

[51] Int. Cl.$^2$ ............... A61K 31/11; C07C 47/48
[52] U.S. Cl. .............................. 424/333; 260/599
[58] Field of Search .......................... 424/333; 260/599

[56] References Cited

U.S. PATENT DOCUMENTS

| | | | |
|---|---|---|---|
| 2,761,873 | 9/1956 | Gregory et al. | 260/599 |
| 3,718,686 | 2/1973 | Chodnekar et al. | 424/308 |
| 3,833,642 | 9/1974 | Chodnekar et al. | 424/308 |
| 3,880,935 | 4/1975 | Chodnekar et al. | 260/613 D |

OTHER PUBLICATIONS

Bauman, J. Org. Chem., vol. 36, No. 3 (1971), pp. 396–398.

*Primary Examiner*—Leonard Schenkman
*Attorney, Agent, or Firm*—L. Ruth Hattan; Eugene O. Retter; George W. Rauchfuss, Jr.

[57] ABSTRACT

Substituted benzaldehydes of the following general structure are useful as hypolipidemic agents:

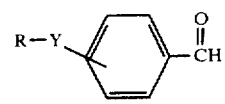

wherein Y is selected from oxygen and divalent sulfur; R is selected from a straight or branched saturated hydrocarbon chain having from 10 to 20 carbon atoms and a straight or branched unsaturated hydrocarbon chain having from 10 to 20 carbon atoms and from 1 to 4 double bonds.

5 Claims, No Drawings

SUBSTITUTED BENZALDEHYDE HYPOLIPIDEMIC AGENTS

This is a continuation of application Ser. No. 619,304, filed Oct. 3, 1975, now U.S. Pat. No. 4,066,788.

FIELD OF THE INVENTION

This invention relates to alkoxy and alkylthio substituted benzaldehyde derivatives useful as hypolipidemic agents.

DESCRIPTION OF PRIOR ART

Compounds described herein, wherein Y is oxygen, are known. The preparation of n-dodecylthiobenzaldehyde is described in J. Org. Chem., 36, 396-8 (1971). To applicant's knowledge, the use of the compounds described herein as hypolipidemic agents has not been described heretofore.

SUMMARY OF INVENTION

Compounds of the following general Formula I are useful as hypolipidemic agents:

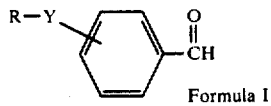

Formula I wherein Y is selected from oxygen and divalent sulfur, and R is selected from a straight or branched saturated hydrocarbon chain having from 10 to 20 carbon atoms and a straight or branched unsaturated hydrocarbon chain having from 10 to 20 carbon atoms and from 1 to 4 double bonds.

DETAILED DESCRIPTION OF THE INVENTION

In the above general Formula I the substituent group represented as R—Y— may be attached at the ortho, meta, or para positions of the benzene ring.

As represented herein, R may be a straight or branched saturated hydrocarbon chain having from 10 to 20 carbon atoms, in which case the substituent group R—Y— may be represented as

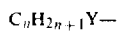

wherein n is an integer of from 10 to 20, and Y is selected from oxygen and divalent sulfur, and the hydrocarbon moiety may be straight or branched. The straight or branched saturated hydrocarbon chain described herein may also be described as a straight or branched alkyl group having from 10 to 20 carbon atoms. The substituent R may also be a straight or branched unsaturated hydrocarbon chain having from 10 to 20 carbon atoms and from 1 to 4 double bonds and may be represented as

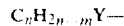

wherein Y is selected from oxygen and divalent sulfur; n is an integer of from 10 to 20; m is the integer 1, 3, 5, or 7 as the number of double bonds increases respectively from 1 to 4 in the hydrocarbon chain, which may be straight or branched. The straight or branched unsaturated hydrocarbon chain described herein may also be described when one double bond is present, as a straight or branched alkenyl group having from 10 to 20 carbon atoms; when two double bonds are present, as a straight or branched alkadienyl group having from 10 to 20 carbon atoms; when three double bonds are present, as a straight or branched alkatrienyl group having from 10 to 20 carbon atoms; and when four double bonds are present, as a straight or branched alkatetraenyl group having from 10 to 20 carbon atoms.

Illustrative examples of straight or branched saturated hydrocarbon chains having from 10 to 20 carbon atoms, which R may represent, are decyl, undecyl, dodecyl, tridecyl, tetradecyl, 3,7-dimethyloctyl, 2,4-diethylnonyl, 1-methylundecyl, pentadecyl, hexadecyl, heptadecyl, octadecyl, 3-methyloctadecyl, nonadecyl, and didecyl. Illustrative examples of straight or branched unsaturated hydrocarbon groups having from 10 to 20 carbon atoms and from 1 to 4 double bonds which R may represent are 10-undecenyl, 9,12-octadecadienyl, 3,7,11-trimethyl-2,6,10-octatrienyl, 3,7-dimethyl-2,6-octadienyl, 5,9-dimethyl-2,4,8-decatrienyl, 3,7-dimethyl-6-octenyl, 1,2,5,9-tetramethyl-2,4,8-decatrienyl, and 11-didecenyl. Both the cis- and trans- isomers of the unsaturated alkyl groups are included within the scope of this invention.

It is apparent from the above general Formula I that the compounds described herein are alkoxy substituted benzaldehydes when the symbol Y is oxygen, and are alkylthio substituted benzaldehydes when the symbol Y is divalent sulfur as represented, respectively, by the following general Formulas II and III.

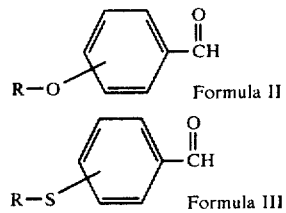

Formula II

Formula III

In the above general Formulas II and III, the substituent group R has the meaning defined hereinabove.

Compounds of general Formula III wherein the substituent group R is selected from a straight or branched saturated hydrocarbon chain having from 13 to 20 carbon atoms and a straight or branched unsaturated hydrocarbon chain having from 13 to 20 carbon atoms and from 1 to 4 double bonds are novel compounds and represent a preferred embodiment of this invention. Of these compounds, those wherein the substituent group R has from 14 to 16 carbon atoms is a more preferred embodiment of this invention. The novel compounds of general Formula III wherein the substituent group R—S— is attached to the meta- or para-positions of the benzene ring is another more preferred embodiment of this invention.

Another embodiment of this invention is the use of the compounds described herein as represented by general Formulas I to III as hypolipidemic agents. The use of the compounds of general Formula II as hypolipidemic agents represents a preferred embodiment of this invention and within this preferred embodiment, the use of the compounds wherein the R substituent has from 12 to 16 carbon atoms is a more preferred embodiment. The use of the compounds of general Formula II wherein the R—O— substituent is attached at the para-position of the benzene ring is another more preferred embodiment of this invention. The use of the compounds of general Formula III as hypolipidemic agents represents another preferred embodiment of this invention and within this preferred embodiment, the use of the compounds wherein the R substituent has from 12 to 16 carbon atoms is a more preferred embodiment. The use of the compounds of general Formula III wherein the R—S— substituent is attached at the para-position of the benzene ring is another more preferred embodiment of this invention.

Illustrative examples of compounds of this invention are 4-decyloxybenzaldehyde, 4-tetradecyloxybenzaldehyde, 4-(trans-9-octadecenyloxy)benzaldehyde, 4-dodecyloxybenzaldehyde, 4-tetradecylthiobenzaldehyde, 3-tetradecyloxybenzaldehyde, 4-octadecyloxybenzaldehyde, 3-dodecylthiobenzaldehyde, 3-tridecyloxybenzaldehyde, 4-hexadecyloxybenzaldehyde, 2-heptadecylthiobenzaldehyde, 4-undecyloxybenzaldehyde, 3-hexadecyloxybenzaldehyde, 3-pentadecylthiobenzaldehyde, 2-tetradecyloxybenzaldehyde, 4-nonadecylthiobenzaldehyde, 4-didecylthiobenzaldehyde, 3-didecyloxybenzaldehyde, 4-dodecylthiobenzaldehyde, 3-tetradecylthiobenzaldehyde, 4-undecylthiobenzaldehyde, 4-(10-undecenylthio)benzaldehyde, 4-(trans,trans-1,2,5,9-tetramethyl-2,4,8-decatrienyloxy)benzaldehyde, 4-(cis-cis-9,12-octadecadienylthio)benzaldehyde, and 3-(3,7-dimethyl-6-octenyloxy)benzaldehyde.

The compounds described herein are useful as hypolipidemic agents in that they reduce blood lipids, particularly cholesterol and triglycerides without concurrent accumulation of desmosterol. These compounds can be administered to animals, mammals, rats, cats, dogs, pigs, cattle, horses and humans and are useful in the treatment of hyperlipidemic states such as are encountered in patients with cardiovascular diseases that can result in heart failure and stroke. As used herein, the term patient is intended to mean the animal or mammal being treated.

To illustrate the utility of the compounds of this invention, young male rats of the Wistar strain initially weighing about 175 grams are given free access to a diet which contains 0.15% by weight of test compounds, that is, a compound of general Formulas I to III. This diet was prepared by mixing the test compound with commercial Purina Chow. (Trademark of Ralston-Purina Company, St. Louis, Mo.). Groups of animals were given these diets for either 4 or 10 days. Control groups of 6 rats each were given Purina Chow to which no test compound had been added. At the end of the treatment period, all rats were bled by cardiac puncture, and the plasma was analyzed for cholesterol and triglyceride content. The results are given in the following Table I.

Table I

| Test Compound: | 4-(tetradecyloxy)-benzaldehyde | 4-(decyloxy)-benzaldehyde |
|---|---|---|
| Duration of Treatment (Days): | 4 | 10 |
| Daily Dose mg/kg (a): | 139 | 153 |
| No. Rats: | 6 | 6 |
| Plasma Cholesterol % Reduction (b): | 25 | 31 |
| Plasma Triglyceridea % Reduction (b): | 62 | 80 |

(a) Determined by measuring food consumption.
(b) Compared to untreated control rats in the same experiment.

The compounds of this invention can be administered orally or parenterally, either alone or in the form of a pharmaceutical preparation. Pharmaceutical preparations containing conventional pharmaceutical carriers and, as active ingredients, compounds of this invention, can be employed in unit dosage forms such as solids, for example, tablets, capsules, and pills, or liquid solutions, suspensions, or emulsions for oral and parenteral administration. The dosage unit administered can be any lipid-lowering effective amount. The quantity of compound administered can vary over a wide range to provide from about 0.5 mg/kg (milligram per kilogram) to about 300 mg/kg of body weight of the patient per day, and preferably from about 10 mg/kg to 30 mg/kg of body weight of the patient per day to achieve the desired effect. Unit doses can contain from about 50 mg to 1 g of a compound described herein and may be administered, for example, from 1 to 4 times daily.

The compounds described herein may be prepared by chemical or catalytic reduction of the corresponding R—Y— substituted carboxylic acid halide or tertiary amide by methods generally described in J. March, *Advanced Organic Chemistry: Reactions, Mechanisms and Structure*, McGraw-Hill, pp. 351, 352 and 684 (1968). Reduction of the the corresponding carboxylic acid halides, for example, the acid chloride, using a catalytic hydrogenation method to give the aldehyde compound is known as the Rosenmund reduction and is the most common way to prepare the aldehydes. A suitable catalyst for this reaction is palladium-BaSO$_4$ in a ratio of 1 part catalyst to 5 to 10 parts of acid chloride. This reaction may be carried out with or without a regulator, such as, quinoline sulfur. Suitable solvents for this reaction are dry solvents selected from aromatic hydrocarbons, such as, benzene, toluene and xylene, non-aromatic hydrocarbons, such as, decalin and ethers, such as, diethylether. This reaction may be carried out at temperatures of from room temperature, that is, about 25° C. to the reflux temperature of the solvent, and the reaction time varies from about 15 minutes to 24 hours.

Reduction of the tertiary carboxamide or acid halide using a metal hydride reducing agent is another way of obtaining the aldehyde compounds. This reaction can be carried out in ether solvents, such as, diethylether, tetrahydrofuran, dioxane and glyme, or, hydrocarbon solvents, such as, benzene and toluene. The reaction temperature may vary from 0° C. to the reflux temperature of the solvent and the reaction time may vary from about 15 minutes to 24 hours.

The corresponding nitrile may also be reduced to give the aldehyde compounds by two principal methods, one such method being known as the Stephen reduction, using hydrochloric acid and tin chloride and the other method employing a metal hydride reducing agent. In the Stephen reduction, ether solvents, such as, diethylether and dioxane can be employed and the ether solvent can be saturated with hydrochloric acid to provide a source of HCl required for the reaction. The reaction can be carried out at temperatures from about 25° C. to the reflux temperature of the solvent, and the reaction time can vary from about 15 minutes to 24 hours. Reduction of the nitrile using a metal hydride reducing agent, such as, LiAlH$_4$ or NaAlH$_2$(OCH$_2$CH$_2$OCH$_3$)$_2$ can be carried out in ether solvents, such as, diethylether, tetrahydrofuran, dioxane and glyme, or hydrocarbon solvents, such as, toluene and benzene. The reaction temperature can vary from 0° C. to the reflux temperature of the solvent, and thre reaction time can vary from about 15 minutes to 24 hours. The reduction reaction is followed by acid hydrolysis by, for example, adding aqueous hydrochloric acid to the reaction mixture. The carboxylic acid halides, carboxamides and nitrile derivatives can be prepared from the corresponding acid by procedures generally known in the art. The carboxamide derivative can be isolated or formed in situ. The corresponding carboxylic acid derivatives can be prepared by several methods, such as, the Williamson reaction, as generally described in the above cited March reference at page 316, as illustrated by the following reaction sequence:

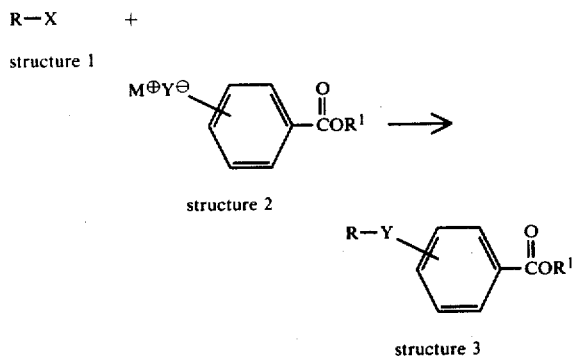

In the above reaction sequence, X represents a halogen atom, such as, chlorine, bromine or iodine; M$^\oplus$ represents a metal salt, such as, lithium, sodium, potassium, silver or mercury; R$^1$ is lower alkyl, such as, methyl and ethyl; and R has the meaning defined in general Formula I. In the compounds of structures 2 and 3 the substituent groups M$^\oplus$Y$^\ominus$- and R—Y— can be attached at the ortho-, meta- or para-positions of the benzene ring. The above reaction may be carried out with or without solvents. Suitable solvents for this reaction include lower alcohols such as ethanol and isopropyl alcohol, or ketones, such as, acetone and methyl isobutyl ketone, or amides, such as, dimethylformamide and dimethylacetamide. Other suitable solvents include dimethylsulfoxide, acetonitrile, and dimethoxyethane. The temperature of the reaction may vary from about 25° C. to the reflux temperature of the solvent, and the reaction time may vary from about 1 hour to 80 hours. The phenoxide metal salts, as represented by the compounds of structure 2, are preferably formed in situ by the addition of a base such as, sodium methoxide, potassium carbonate, or potassium hydroxide to the corresponding hydroxy phenyl or mercapto phenyl derivative. The esters of structure 3 are hydrolyzed to the corresponding carboxylic acids by procedures generally known in the art.

In the above reaction in place of the compounds as represented by structure 1 R-methane sulfonates and R-p-toluene sulfonates wherein R has the meaning defined in general Formula I may be used.

The corresponding benzoic acid derivatives may also be prepared by displacement of a leaving group of a benzoate compound with a metal alkoxide or metal thioalkoxide as illustrated by the following:

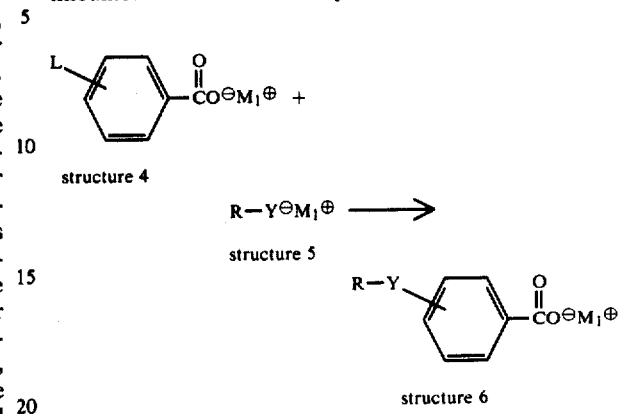

In the above reaction, L represents a leaving group, such as, a diazo salt or a halide such as bromide or iodide; M$_1$$^\oplus$ represents a metal salt, such as, potassium, sodium, or lithium; and R and Y have the meanings defined in general Formula I. The above illustrated displacement may be carried out in the absence of a solvent resulting in a fusion reaction, or in the presence of a high boiling inert solvent such as dimethylformamide, dimethylsulfoxide or dimethylacetamide. The salts of structure 6 are acidified to give the corresponding carboxylic acids.

The above described Williamson ether reaction can also be employed to prepare the aldehyde derivatives described herein, as illustrated by the following reaction sequence:

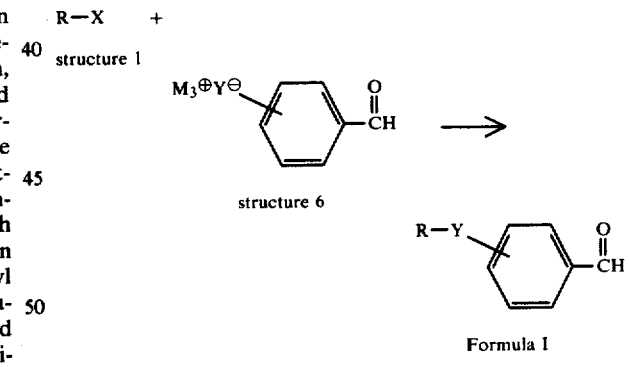

In the above reaction sequence, R and Y have the meanings defined in general Formula I; X is as defined hereinabove; and M$_3$$^\oplus$ represents a metal salt, such as, lithium, calcium potassium, sodium, silver, and mercury. The M$_3$$^\oplus$—Y$^\ominus$— and the R—Y— substituents in structure 7 and Formula I respectively may be attached at the ortho-, meta- or para-positions of the phenyl ring. The reaction conditions for this ether synthesis are the same as described hereinabove for the preparation of the compounds of structure 3.

The following specific examples are illustrative of the compounds described herein.

EXAMPLE 1

4-(Decyloxy)benzaldehyde

To a mixture of 27.8 g (0.1 mole) of 4-(decyloxy)benzoic acid in 500 ml of tetrahydrofuran cooled to 0° C. is slowly added 16.2 g (0.1 mole) of N,N'-carbonyldiimidazole. The mixture is heated to reflux for 1 hour then cooled to −20° C. To the cooled mixture is added 1.9 g (0.05 mole) of lithium aluminum hydride and stirring is continued at −20° C. for 1 hour. To the reaction mixture is slowly added 100 ml of 5% aqueous hydrochloric acid followed by the addition of ether. The ether layer is separated and washed with 5% aqueous hydrochloric acid, water, and 5% aqueous sodium bicarbonate then dried over sodium sulfate, filtered and evaporated to dryness to give 4-(decyloxy)benzaldehyde.

EXAMPLE 2

4-Tetradecyloxybenzaldehyde

To a stirred mixture of 50 g (0.41 mole) of p-hydroxybenzaldehyde, 22.2 g (0.41 mole) of sodium methoxide and 500 ml of dried dimethylformamide was added 114 g (0.41 mole) of 1-bromotetradecane. The mixture was refluxed for 3 hours, then allowed to stand at room temperature overnight after which it was poured into ice-water and extracted with diethyl ether. The ether layer was washed with water, 5% potassium hydroxide, and saline, and dried over sodium sulfate, filtered and evaporated. The residue is recrystallized from hexane to give 4-tetradecyloxybenzaldehyde.

EXAMPLE 3

When in the procedure of Example 1 an appropriate amount of 4-tetradecyloxybenzoic acid, 4-(cis,cis-9,12-octadecadienylthio)benzoic acid, 3-tetradecylthiobenzoic acid, 3-hexadecylthiobenzoic acid, 3-octadecylthiobenzoic acid, 3-didecylthiobenzoic acid, or 3-tridecylthiobenzoic acid is substituted for 4-decyloxybenzoic acid the following respective products are obtained:
4-tetradecyloxybenzaldehyde,
4-(cis,cis-9,12-octadecadienylthio)benzaldehyde,
3-tetradecylthiobenzaldehyde,
3-hexadecylthiobenzaldehyde,
3-octadecylthiobenzaldehyde,
3-didecylthiobenzaldehyde, and
3-tridecylthiobenzaldehyde.

When in the procedure of Example 2 appropriate amounts of an alkyl halide and an aldehyde listed in the following Table II are substituted respectively for 1-bromotetradecane and p-hydroxybenzaldehyde the respective products listed in Table II are obtained.

TABLE II

| ALKYL HALIDE | ALDEHYDE | PRODUCT |
|---|---|---|
| 1-chlorodecane | o-mercaptobenzaldehyde | 2-decylthiobenzaldehyde |
| 1-bromoundecane | m-hydroxybenzaldehyde | 3-undecyloxybenzaldehyde |
| 1-bromododecane | m-hydroxybenzaldehyde | 3-dodecyloxybenzaldehyde |
| 1-bromotridecane | p-mercaptobenzaldehyde | 4-tridecylthiobenzaldehyde |
| 1-bromotetradecane | o-mercaptobenzaldehyde | 2-tetradecylthiobenzaldehyde |
| 1-bromopentadecane | o-hydroxybenzaldehyde | 2-pentadecyloxybenzaldehyde |
| 1-chlorohexadecane | p-mercaptobenzaldehyde | 4-hexadecylthiobenzaldehyde |
| 1-bromoheptadecane | m-hydroxybenzaldehyde | 3-heptadecyloxybenzaldehyde |
| 1-bromooctadecane | p-mercaptobenzaldehyde | 4-octadecylthiobenaldehyde |
| 1-bromononadecane | p-hydroxybenzaldehyde | 4-nonadecyloxybenzaldehyde |
| 1-bromodidecane | p-mercaptobenzaldehyde | 4-didecylthiobenzaldehyde |
| 1-bromo-3,7-dimethyl-6-octene | p-hydroxybenzaldehyde | 4-(3,7-dimethyl-6-octenyloxy)benzaldehyde |
| 1-chloro-2-decene | o-hydroxybenzaldehyde | 2-(2-decenyloxy)benzaldehyde |
| 1-bromo-10-undecene | p-hydroxybenzaldehyde | 4-(10-undecenyloxy)benzaldehyde |
| 1-bromo-1,2,5,9-tetramethyl-2,4,8-decatriene | p-mercaptobenzaldehyde | 4-(trans,trans-1,2,5,9-tetramethyl-2,4,8-decatrienylthio)benzaldehyde |
| 1-bromo-3-methyloctadecane | o-mercaptobenzaldehyde | 2-(3-methyloctadecylthio)benzaldehyde |

The following Examples are illustrative of pharmaceutical formulations of the compounds described herein.

An illustrative composition for tablets is as follows:

| | Per Tablet |
|---|---|
| (a) 4-decyloxybenzaldehyde | 100.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

An illustrative composition for a parenteral injection is the following wherein the quantities are on a weight to volune basis.

| | Amount |
|---|---|
| (a) 4-tetradecyloxybenzaldehyde | 100.0 mg |
| (b) peanut oil | 1 ml |

The active ingredient is suspended in the oil, and to the suspension is added an appropriate amount of a preservative such as methylparaben or propylparaben.

An illustrative composition for hard gelatin capsules is as follows:

| | Amount |
|---|---|
| (a) 3-tetradecylthiobenzaldehyde | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

We claim:

1. A pharmaceutical composition in unit dosage form containing about 50 milligrams to 1 gram of a compound of the formula:

wherein R is a straight saturated hydrocarbon chain having from 13 to 20 carbon atoms or a straight unsaturated hydrocarbon chain having from 13 to 20 carbon atoms and from 1 to 4 double bonds and a significant amount of a pharmaceutical carrier.

2. The composition of claim 1 wherein R has from 14 to 16 carbon atoms.

3. A compound of the formula:

wherein R is a straight saturated hydrocarbon chain having from 13 to 20 carbon atoms or a straight unsaturated hydrocarbon chain having from 13 to 20 carbon atoms and from 1 to 4 double bonds.

4. A compound of claim 3 wherein R is a straight saturated hydrocarbon chain having 14 carbon atoms.

5. A compound of claim 3 wherein R is a straight saturated hydrocarbon chain having 16 carbon atoms.